(12) United States Patent
Xie et al.

(10) Patent No.: US 6,736,508 B2
(45) Date of Patent: May 18, 2004

(54) TRACKING ASSISTED OPTICAL PROCEDURE

(75) Inventors: Jing-Gang Xie, Pleasanton, CA (US); Markus Kohnle, Aalen (DE); Jay Wei, Fremont, CA (US)

(73) Assignee: Carl Zeigs Medike, Inc., Dublin, CA (US)

( * ) Notice: Subject to any disclaimer, the term of this patent is extended or adjusted under 35 U.S.C. 154(b) by 0 days.

(21) Appl. No.: 10/206,423

(22) Filed: Jul. 26, 2002

(65) Prior Publication Data

US 2003/0160943 A1 Aug. 28, 2003

Related U.S. Application Data

(63) Continuation-in-part of application No. 10/086,092, filed on Feb. 26, 2002.

(51) Int. Cl.$^7$ .............................................. A61B 3/14
(52) U.S. Cl. .................................................. 351/209
(58) Field of Search ............................ 351/205, 209, 351/210, 200, 221, 245, 208; 356/496, 498, 500, 501, 450; 600/476, 477, 481; 606/4, 5

(56) References Cited

U.S. PATENT DOCUMENTS

| | | | |
|---|---|---|---|
| 5,321,501 A | 6/1994 | Swanson et al. | ............ 356/345 |
| 5,446,545 A | * 8/1995 | Taylor | ......................... 356/501 |
| 5,459,570 A | 10/1995 | Swanson et al. | ............ 356/345 |
| 5,506,634 A | 4/1996 | Wei et al. | ..................... 351/221 |
| 5,644,642 A | 7/1997 | Kirschbaum | ................ 382/103 |
| 5,767,941 A | 6/1998 | Ferguson | .................... 351/206 |
| 6,325,512 B1 | 12/2001 | Wei | .............................. 351/209 |

OTHER PUBLICATIONS

"400–Hz mechanical scanning optical delay line" by K. F. Kwong et al., *Optics Letters*, vol. 18, No. 7, Apr. 1, 1993, pp. 558–560.

"High–speed phase– and group–delay scanning with a grating–based phase control delay line" by G. J. Tearney et al., *Optics Letters*, vol. 22, No. 23, Dec. 1, 1997, pp. 1811–1813.

"Computer–assisted laser photocoagulation of the retina–a hybrid approach" by E. Naess et al., *J. of Biomedical Optics*, 7(2) Apr., 2002, pp. 179–189.

* cited by examiner

*Primary Examiner*—George Manuel
(74) *Attorney, Agent, or Firm*—Michael B. Einschlag

(57) ABSTRACT

One embodiment of the present invention is an optical coherence tomography ("OCT") application apparatus that performs an OCT application on an object. The OCT application apparatus includes: (a) an OCT scanning apparatus which outputs a scanning beam of OCT scanning radiation; and (b) an active tracking system that generates and scans a tracking beam of tracking radiation in a predetermined pattern over a region; wherein the active tracking system includes an analysis system that: (i) when the object is at a calibration position, scans the tracking beam about an irregular reference tracking feature in the region, and detects a calibration retro-reflected tracking beam to form calibration information; (ii) after the calibration information is formed, scans the tracking beam over the region, detects a displacement retro-reflected tracking beam, and analyzes the detected displacement retro-reflected tracking beam together with the calibration information to detect movement of the object; (iii) generates tracking signals; and (iv) applies the tracking signals to a tracking mechanism system to cause the tracking beam and the scanning beam to follow movement of the object.

29 Claims, 6 Drawing Sheets

Acquiring Xc and Yc at center position

Acquiring Xd and Yd at displaced position

TRACKING ASSISTED OPTICAL PROCEDURE

This is a continuation-in-part of a patent application entitled "Tracking Assisted Optical Coherence Tomography" having Ser. No. 10/086,092 which was filed on Feb. 26, 2002.

TECHNICAL FIELD OF THE INVENTION

One or more embodiments of the present invention relate to method and apparatus for performing an optical coherence tomographic examination of tissue such as an eye. In particular, the one or more embodiments of the present invention relate to method and apparatus for performing an optical coherence tomographic examination of an eye using an active tracking system to lock an optical coherence tomography ("OCT") scanning beam on desired features in retinal tissue for use, for example and without limitation, in imaging retinal tissue, measuring retinal and retinal nerve fiber layer thickness, mapping the topography of the optic nerve head, and so forth. In addition, one or more further embodiments of the present invention relate to method and apparatus for performing optical procedures using an active tracking system to lock an optical beam on desired features, such optical procedures including laser surgical applications such as, for example and without limitation, laser photocoagulation procedures, laser refractive surgical procedures (for example, laser corneal ablation procedures), and so forth.

BACKGROUND OF THE INVENTION

As is well known, an optical coherence tomography ("OCT") apparatus (for example, as disclosed in U.S. Pat. No. 5,321,501 ("the '501 patent")) is an optical imaging apparatus that can perform micron-resolution, cross-sectional imaging (also referred to as tomographic imaging) of biological tissue. As is also well known, to make measurements along an axial direction (i.e., along a direction into the biological tissue): (a) radiation is directed to, and reflected by, a reference mirror located in one arm (a reference arm) of a Michelson interferometer (the position of the reference mirror is scanned); and (b) in a second arm (a sample arm) of the Michelson interferometer, radiation is directed to, and scattered by, the biological tissue. Whenever the optical path difference of radiation in the two arms of the Michelson interferometer is equal to, or is less than, the optical coherence length of the radiation transmitted into the interferometer from a source, an optical interference signal can be detected. As disclosed in the '501 patent, a cross-sectional image of the tissue is formed by combining data from serial axial scans.

The length of time it takes to produce a tomographic image is limited by several factors: (a) the scan speed of the reference mirror in the reference arm used to obtain measurements in the axial direction; (b) the transverse scan speed of deflectors used to acquire serial axial scans; (c) signal-to-noise limits related to image quality; and (d) the speed of electronics, and any associated computer, in sampling analog OCT signals and transforming them into a pseudo color, or gray scale, image. However, in general, as the scan speed of the reference mirror goes up (to more rapidly obtain axial scans), the signal-to-noise ratio goes down; thereby adversely affecting image quality. On the other hand, as one can readily appreciate, when imaging tissue in an eye, one is constrained to obtain images rapidly to avoid problems caused by eye movement.

At present, the scan speed of the reference mirror is a limiting factor in OCT image acquisition. To understand this, refer to U.S. Pat. No. 5,459,570 ("the '570 patent") where the reference mirror is moved by a PZT actuator. Although the scan speed of a PZT actuator can be as high as several KHz, the scan range is limited to the micron range, which micron range is not practical for in vivo human eye diagnosis where a scan range of a couple of millimeters is required for clinical use. Although the required several millimeter scan range can be obtained by mounting a retro-reflector on one end of an arm that is scanned by a galvanometer, the scan speed is limited to about a few hundred hertz (this scan method is currently employed in a commercially available OCT scanner device made by Zeiss Humphrey Systems of Dublin Calif.).

A scan device in an OCT system that provides a two to four KHz scan speed with a useful scan range was disclosed in an article entitled "High-speed phase-and group-delay scanning with a grating-based phase control delay line" by G. J. Tearney et al. in *Optics Letters*, Vol. 22, No. 23, Dec. 1, 1997, pp. 1811–1813, which scan device was based on a phase ramping delay line principle disclosed in an article entitled "400-Hz mechanical scanning optical delay line" by K. F. Kwong et al. in *Optics Letters*, Vol. 18, No. 7, Apr. 1, 1993, pp. 558–560. A disadvantage of the scan device disclosed in the G. J. Tearney et al. article is that it is easily worn out, and there is an upper limit light power allowed for safe use in in-vivo human eye diagnosis. However, as pointed out above, with increasing scan speed, the signal-to-noise ratio will be reduced, and image quality will deteriorate.

Although OCT scan data can be used to provide tomographic images of tissue such as an eye, the OCT data obtained has many uses other than in providing an image. For example, applications of OCT data include measuring retinal and retinal nerve fiber layer thickness, mapping the topography of the optic nerve head, and so forth. However, in these applications, similar problems arise, i.e., how to obtain data having acceptable signal-to-noise ratios while taking into account movement of the tissue. In light of the above, there is a need for a method and apparatus that can obtain high quality OCT data, for example, to form tomographic scan images, while taking into account the issue of, for example, patient movement.

SUMMARY OF THE INVENTION

One or more embodiments of the present invention advantageously satisfy one or more of the above-identified needs in the art, and provide method and apparatus for performing optical procedures such as, for example, and without limitation, optical coherence tomography ("OCT") applications. Specifically, one embodiment of the present invention is an OCT application apparatus that performs an OCT application on an object, which OCT application apparatus comprises: (a) an OCT scanning apparatus which outputs a scanning beam of OCT scanning radiation; and (b) an active tracking system that generates and scans a tracking beam of tracking radiation in a predetermined pattern over a region; wherein the active tracking system comprises an analysis system that: (i) when the object is at a calibration position, scans the tracking beam about an irregular reference tracking feature in the region, and detects a calibration retro-reflected tracking beam to form calibration information; (ii) after the calibration information is formed, scans the tracking beam over the region, detects a displacement retro-reflected tracking beam, and analyzes the detected displacement retro-reflected tracking beam together with the calibration information to detect movement of the object; (iii) generates tracking signals; and (iv) applies the tracking signals to a tracking mechanism system to cause the tracking beam and the scanning beam to follow movement of the object.

DETAILED DESCRIPTION

In accordance with one or more embodiments of the present invention, high resolution, tomographic images of features of, for example, a human eye are obtained by performing relatively slow optical coherence tomography ("OCT") scans. For example, some patients can keep an eye open for as long as ten (10) seconds. Advantageously, in accordance with one or more such embodiments of the present invention, the signal-to-noise ratio of images generated by performing such slow scans is higher that that obtained using relatively a rapid scan characteristic of the prior art since the signal-to-noise ratio of the OCT images decreases as the speed of the scan increases.

To perform a relatively slow scan in accordance with one or more embodiments of the present invention, a beam of OCT scanning radiation is locked onto a reference tracking feature to avoid artifacts that might occur due to patient eye movement. In accordance with one or more such embodiments of the present invention, the OCT scan beam is locked onto the reference tracking feature by an active tracking system, which active tracking system utilizes a reflectance characteristic of the reference tracking feature to provide a tracking signal. Advantageously, such an active tracking system can operate at rates which are required for in-vivo human eye tracking rates, i.e., at rates as high as several KHz.

Although one or more embodiments of the present invention are described with reference to providing OCT tomographic images, those of ordinary skill in the art will readily appreciate that such embodiments of the present invention are not limited to those wherein OCT tomographic images are produced. In particular, it is within the scope of the present invention to include embodiments wherein OCT data is obtained for uses other than and/or in conjunction with images such as, for example and without limitation, measuring retinal and retinal nerve fiber layer thickness, mapping the topography of the optic nerve head, and so forth. Thus, an apparatus to perform any of these applications will be referred to herein as an OCT application apparatus, and a method to perform any of these applications will be referred to herein as an OCT application method. Further, although one or more embodiments of the present invention can be utilized with OCT application apparatus to enable a slow scan, further embodiments exist which can be utilized with a rapid scan.

Figure 1:
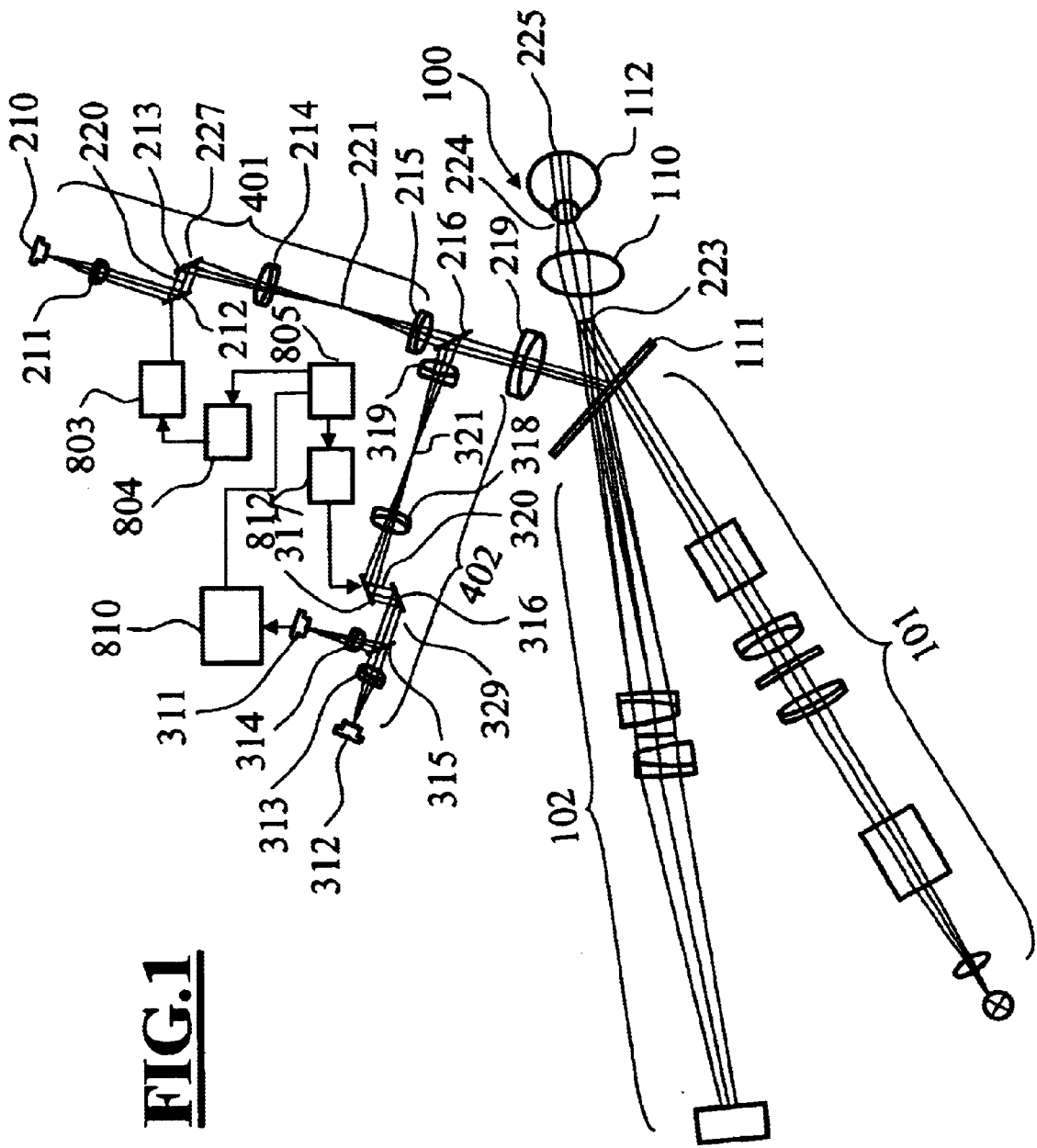
FIG. 1 shows a diagram of a portion of an embodiment of the present invention, and various optical paths associated therewith.

FIG. 1 shows a diagram of a portion of embodiment 100 of the present invention, and various optical paths associated therewith. As shown in FIG. 1, embodiment 100 comprises fundus illumination apparatus 101, viewing apparatus 102, active tracking system 402, and OCT scanning arm 401 of an OCT apparatus (in particular, OCT scanning arm 401 comprises a sample arm of an OCT scanning apparatus). The rest of the OCT apparatus (not shown) is fabricated in accordance with any one of a number of methods that are well known to those of ordinary skill in the art, and is not shown to make it easier to understand one or more embodiments of the present invention.

An embodiment of fundus illumination apparatus 101 and an embodiment of viewing apparatus 102 are disclosed in U.S. Pat. No. 5,506,634, which patent is assigned to the assignee of the present application, and which patent is incorporated herein by reference. As seen in FIG. 1, the optical path of fundus illumination apparatus 101 and the optical path of viewing apparatus 102 are combined by beamsplitter 111, and aerial image plane 223 is relayed onto retina 225 of eye 112 by ocular lens system 110 (as is well known to those of ordinary skill in the art, ocular lens system 110 may comprise one or more lenses) and the lens of eye 112.

FIG. 1 further shows: (a) an optical path of a beam of tracking radiation (a "tracking beam") output from active tracking system 402, and (b) an optical path of a beam of OCT scanning radiation (a "scanning beam") output from OCT scanning arm 401. As shown in FIG. 1, the scanning beam output from a face end of, for example, and without limitation, fiber interferometer 210, passes through collimating lens system 211 (as is well known to those of ordinary skill in the art, lens system 211 may comprise one or more lenses), and impinges upon scanning mechanism 227. As is well known to those of ordinary skill in the art, OCT scanning radiation is typically output from a short coherence length source such as, for example, and without limitation, a superluminescent diode. As further shown in FIG. 1, scanning mechanism 227 comprises a pair of scanning mirrors 212 and 213 that are driven, for example, and without limitation, by scan driver 803 which is driven, in turn, by signals output from control module 804. In accordance with one such embodiment, scanning mirrors 212 and 213 are reflectors that are orthogonally mounted on, for example, and without limitation, a pair of X-Y galvanometers, in accordance with any one of a number of methods that are well known to those of ordinary skill in the art.

As is well known to those of ordinary skill in the art, scanning mirrors pair 212 and 213 is used to generate a desired scan pattern on retina 225 to form an OCT image. A typical OCT scan pattern in a direction perpendicular to an axial scan direction is a line or a circle. In such a case, in accordance with this embodiment of the present invention, scanning mirrors pair 212 and 213 is activated to produce a scan pattern which is a line or a circle.

In accordance with this embodiment of the present invention, scanning pivot point 220 of scanning mirrors pair 212 and 213 (i.e., a middle point between scanning mirrors pair 212 and 213) is optically conjugated to pupil 224 of eye 112 by (a) one-to-one magnification, relay lens system pair 214 and 215; and (b) lens system 219 and ocular lens system 110. Thus, as was described in U.S. Pat. No. 5,506,634, there will be no vignetting in the OCT scanning beam. As is well known to those of ordinary skill in the art, lens systems 214, 215, and 219 may each comprise one or more lenses.

As shown in FIG. 1, an embodiment of active tracking system 402 comprises tracking beam radiation source 312 which is, for example, and without limitation, a laser or a light emitting diode ("LED"), or any one of a number of other coherent or incoherent sources of radiation. The tracking beam output from tracking beam radiation source 312 is collimated by collimating lens system 313 (as is well known to those of ordinary skill in the art, lens system 313 may comprise one or more lenses). The collimated tracking beam passes through beamsplitter 315, and impinges upon dither mechanism 329. As further shown in FIG. 1, dither mechanism 329 comprises a pair of dithering mirrors 316 and 317 that are driven, for example, and without limitation, by dither driver 812. Dither driver 812 is driven, in turn, by signals output from control module 805. In accordance with one such embodiment, dithering mirrors 316 and 317 are reflectors that are orthogonally mounted on, for example, and without limitation, a pair of X-Y galvanometers in accordance with any one of a number of methods that are well known to those of ordinary skill in the art (for example, galvanometers with low armature inertia can be used to achieve a high-speed tracking response).

In accordance with this embodiment of the present invention, dithering pivot point 320 of dithering mirrors pair 316 and 317 (i.e., a middle point between dithering mirrors pair 316 and 317) is optically conjugated to pupil 224 of eye 112 by (a) one-to-one magnification, relay lens system pair 318 and 319; and (b) lens system 219 and ocular lens system 110. Thus, as was described in U.S. Pat. No. 5,506,634, there will be no vignetting in the tracking beam. As is well known to those of ordinary skill in the art, lens systems 318 and 319 may each comprise one or more lenses.

In accordance with this embodiment of the present invention: (a) the collimated scanning beam output from scanning mirrors pair 212 and 213 is focused by lens system 214 to point 221; (b) point 221 is optically conjugated to aerial image plane 223 by relay lens system pair 215 and 219; and (c) aerial image plane 223 is optically conjugated to retina 225 of eye 112 by ocular lens system 110 and the lens of eye 112. In addition, in accordance with this embodiment of the present invention: (a) the collimated tracking beam output from dithering mirrors pair 316 and 317 is focused by lens system 318 to point 321; (b) point 321 is optically conjugated to aerial image plane 223 by relay lens system pair 319 and 219; and (c) aerial image plane 223 is optically conjugated to retina 225 of eye 112 by ocular lens system 110 and the lens of eye 112.

As one of ordinary skill in the art will readily appreciate, the tracking beam impinges upon retina 225, and retina 225 retro-reflects at least a portion of the tracking beam. The retro-reflected tracking beam is directed (through the same optical path that brought the tracking beam to eye 112 in the first place) to beamsplitter 315. Beamsplitter 315 directs at least a portion of the retro-reflected tracking beam to impinge upon lens system lens 314 (as is well known to those of ordinary skill in the art, lens system 314 may comprise one or more lenses), and lens system 314 focuses the retro-reflected tracking beam upon photodetector 311 (for example and without limitation, a photodiode).

In accordance with one or more embodiments of the present invention, motion of eye 112 is detected by sensing changes in reflectance (at the wavelengths of the tracking radiation) between a reference tracking feature, and its surrounding or adjacent area. The reference tracking feature may be associated with an eye, or it may be a retro-reflecting material. However, many retinal features have a high enough reflectivity contrast with respect to the background area to be suitable for use as reference tracking features. For example, a reference tracking feature comprising an intersection of three blood vessels in the retina presents a relatively dark area when compared to surrounding retinal tissues. As another example, a reference tracking feature comprising the optical nerve head presents a relatively bright disk when compared to surrounding retinal tissues.

In accordance with this embodiment of the present invention, active tracking system 402 projects the tracking beam onto a reference tracking feature on the retina. Then, as eye 112 moves, due to reflectance differences between the reference tracking feature and the surrounding area, the intensity of the retro-reflected tracking beam detected by photodetector 311 will change. Further, in accordance with this embodiment of the present invention, the direction of motion is detected by detecting changes in reflected radiation intensity, and a tracking signal is generated to drive scanning mirrors pair 212 and 213 and dithering mirrors pair 316 and 317 to track the motion of eye 112.

In accordance with one or more embodiments of the present invention, a mechanism for sensing the direction of motion of eye 112, are fabricated by improving upon a disclosure in U.S. Pat. No. 5,767,941 ("the '941 patent"), which '941 patent is incorporated by reference herein. In accordance with one or more embodiments of the present invention, active tracking system 402 locks onto a reference tracking feature by inducing small, periodic, transverse oscillations or dithers in the tracking beam. The tracking beam radiation may comprise any wavelength of radiation that can be used to detect changes in reflectance between the reference tracking feature and the surrounding area. In particular, the tracking beam may be formed using radiation output from a light emitting diode, or from any one of a number of other incoherent or coherent sources of radiation. Typically, the reference tracking feature is locked onto by the tracking beam in two dimensions with a circular dither.

As shown in FIG. 1, active tracking system 402 includes a reflectometer (beamsplitter 315, lens system 314, and photodetector 311) positioned in an optical path of the retro-reflected tracking beam to provide a reflectometer output signal having a phase corresponding to the phase of the retro-reflected tracking beam. Whenever the tracking beam traverses a region of changing reflectance, a corresponding variation in intensity of the reflectometer output signal occurs. The reflectometer output signal varies synchronously (when appropriately corrected for phase shifts) with the oscillatory motion caused by dither mechanism 329.

As shown in FIG. 1, active tracking system 402 includes signal conditioning module 810. The signal output from photodetector 311 is applied as input to signal conditioning module 810. In accordance with one embodiment of the resent invention, signal conditioning module comprises conventional electronics that conditions the signal for further processing in accordance with any one of a number of methods that are well known to those of ordinary skill in the art, for example, and without limitation, by amplification. The conditioned signal is then applied as input to control module 805. In response, control module 805 generates: (a) tracking signals (the tracking signals are applied as input to control module 804); and (b) dither drive signals (the dither drive signals are applied as input to dither driver 812). In response to the dither drive signals, dither driver 812 causes dither mechanism 329 to: (a) dither the tracking beam in a first and a second direction with, for example, an oscillatory motion having a first phase and a second phase respectively (the first and second phases of oscillatory motion may be orthogonal to each other); and (b) track the motion of eye 112 (i.e., to control the position of the tracking beam relative to the reference tracking feature). In accordance with this embodiment of the present invention, dither mechanism 329 produces a circular dither at the reference tracking feature whenever the oscillatory motions in the first and second directions have identical amplitudes, and have a phase difference of 90 degrees.

In addition, in response to the tracking signals applied as input from control module 805, control module 804 generates scanning drive signals that are applied as input to scan driver 803. In response to the scanning drive signals, scan driver 803 causes scanning mechanism 227 to: (a) control the position of the OCT scanning beam in accordance with predetermined scanning algorithms; and (b) track the motion of eye 112 (i.e., to control the position of the scanning beam relative to the reference tracking feature).

As will be described below in conjunction with FIG. 2, control module 805: (a) compares the phase of the conditioned reflectometer output signal with the phases of signals that caused the dither motion, and (b) generates first and second direction control signals that are coupled to dither driver 812. In response to the first and second direction control signals, dither driver 812 causes dithering mechanism 329 to react so that the tracking beam tracks relative to the reference tracking feature. As described in the '941 patent, the phase comparison produces first and second phase comparison signals that comprise DC offset voltages that are proportional to the amplitude of the components of the reflectometer signal which are in phase with the dither signals. These DC offset voltages are vector correction or error voltages that are proportional to the displacement from equilibrium per dither cycle.

As set forth in the '941 patent, a tracking velocity of the corrections is proportional to the product of a dither frequency of the dither drivers of the dither mechanism and a spatial dimension of the reference tracking feature. The useful dither frequency depends upon several factors. For example, if the beam of tracking radiation is imaged on the retina of an eye at unit magnification, a 2 KHz dither frequency will correspond to approximately a 50μ displacement per dither cycle at a target velocity of 10 cm/sec (i.e., greater than 300 degrees/sec in an eye). Such a dither frequency is sufficient to track a beam of OCT scanning radiation with a spot size of approximately 400μ.

Figure 2:
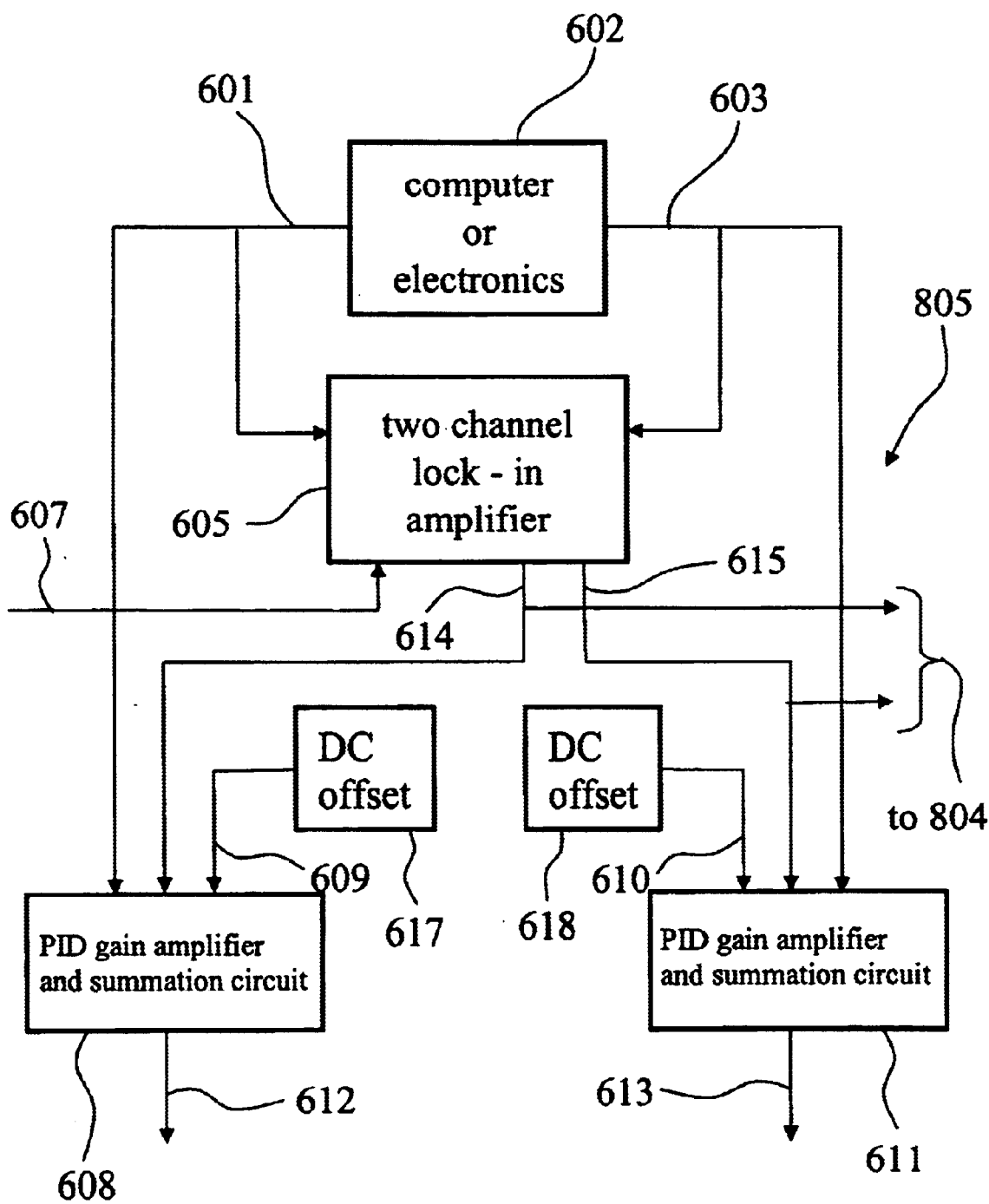
FIG. 2 is a functional block diagram of control module 805 that is fabricated in accordance with one embodiment of the present invention for use in the embodiment shown in FIG. 1.

FIG. 2 is a functional block diagram of control module 805 that is fabricated in accordance with one embodiment of the present invention. As shown in FIG. 2, computer 602 (or conventional electronics circuit 602) generates synchronized cosine signal 601 (i.e., cos(ωt) and sine signal 603 (i.e., sin(ωt) having circular frequency ω in accordance with any one of a number of methods that are well known to those of ordinary skill in the art. Cosine signal 601 is applied as input to dual channel, lock-in amplifier 605 (one could also use a pair of lock-in amplifiers) as an X-reference signal, and sine signal 603 is applied as input to dual channel, lock-in amplifier 605 as a Y-reference signal. For sake of understanding this embodiment, assume that conditioned reflectometer output signal 607 has a time dependence that is given by cos(ωt−φ), where φ is a phase related to a displacement direction of a dithering circle from a reference tracking feature as disclosed in the '941 patent. As shown in FIG. 2, conditioned reflectometer output signal 607 is applied as input to dual channel, lock-in amplifier 605. In response, dual channel, lock-in amplifier 605 generates: (a) X position error signal 614 that is proportional to cos(φ); and (b) generates Y position error signal 615 that is proportional to sin(φ). In essence, dual channel, lock-in amplifier 605 determines the phase variation between: (a) the X-reference signal (cos(ωt) and the Y-reference signal (sin(ωt)) that drive dither scanner 812; and (b) the conditioned reflectometer signal that is proportional to cos(ωt−φ). It does this by expanding terms of the type cos(ωt)cos(ωt−φ) and sin(ωt)cos(ωt−φ), integrating over a predetermined time period (to emulate the effect of integrating from −∞ to +∞), and low pass filtering the result to determine the X position error signal (proportional to cos(φ)) and the Y position error signal (proportional to sin(φ))) as DC offsets. It should be clear to those of ordinary skill in the art that embodiments of the present invention are not limited to the use of a dual channel, lock-in amplifier. In fact, further embodiments exist wherein the above-described operations may be carried out using, for example, a computer such as a personal computer or a digital signal processor ("DSP").

As further shown in FIG. 2: (a) X position error signal 614, cosine signal 601, and DC offset signal 609 are applied as input to PID gain amplifier and summation circuit 608; and (b) Y position error signal 615, sine signal 603, and DC offset signal 610 are applied as input to PID gain amplifier and summation circuit 611. DC offset signals 609 and 610 may be used, for example, and without limitation, to: (a) calibrate embodiment 100; (b) set up initial X and Y offset positions for the tracking beam with respect to the scanning beam; and (c) reset embodiment 100 to adjust for drifts over time due to temperature variation, or other reasons. DC offset signals 609 and 610 are generated by DC offset modules 617 and 618, respectively, in accordance with any one of a number of methods that are well known to those of ordinary skill in the art (for example, using conventional electronics or a computer such as, for example, a personal computer), and DC offset signals 609 and 610 may be varied in response to user input in accordance with any one of a number of methods that are well known to those of ordinary skill in the art. It should also be understood that appropriate scale factors may be applied to X position error signal 614 and Y position error signal 615, respectively, which scale factors may be determined by calibrating embodiment 100 to ensure that the tracking beam follows the reference tracking feature.

As is well known, PID gain amplifier summation circuits 608 and 611, in response to predetermined parameters, add their three inputs and generate signals 612 and 613, respectively, as output. The predetermined parameters: (a) enable PID gain amplifier summation circuits 608 and 611 to integrate the respective error signals over a predetermined length of time to identify and ignore short-lived changes, and thereby, prevent jitter from affecting the system; and (b)

enable PID gain amplifier summation circuits 608 and 611 to take the derivative of the respective error signals so that the respective error signals can be ignored when their rate of change is larger than a predetermined amount, and thereby, prevent jitter from affecting the system.

Signals 612 and 613 output from PID gain amplifier summation circuits 608 and 611, respectively, are applied as input to dither scanner 812. Thus, in accordance with one embodiment of the present invention, signal 612 is applied as input to a galvanometer that drives the X-direction dithering mirror of the pair of mirrors 316 and 317, and signal 613 is applied as input to a galvanometer that drives the Y-direction dithering mirror of the pair of mirrors 316 and 317. In response, the X-direction dithering mirror dithers the tracking beam along the X direction, and causes the tracking beam to follow the motion of the eye along the X direction. In addition, the Y-direction dithering mirror dithers the tracking beam along the Y direction, and causes the tracking beam to follow the motion of the eye along the Y direction.

Figure 3:
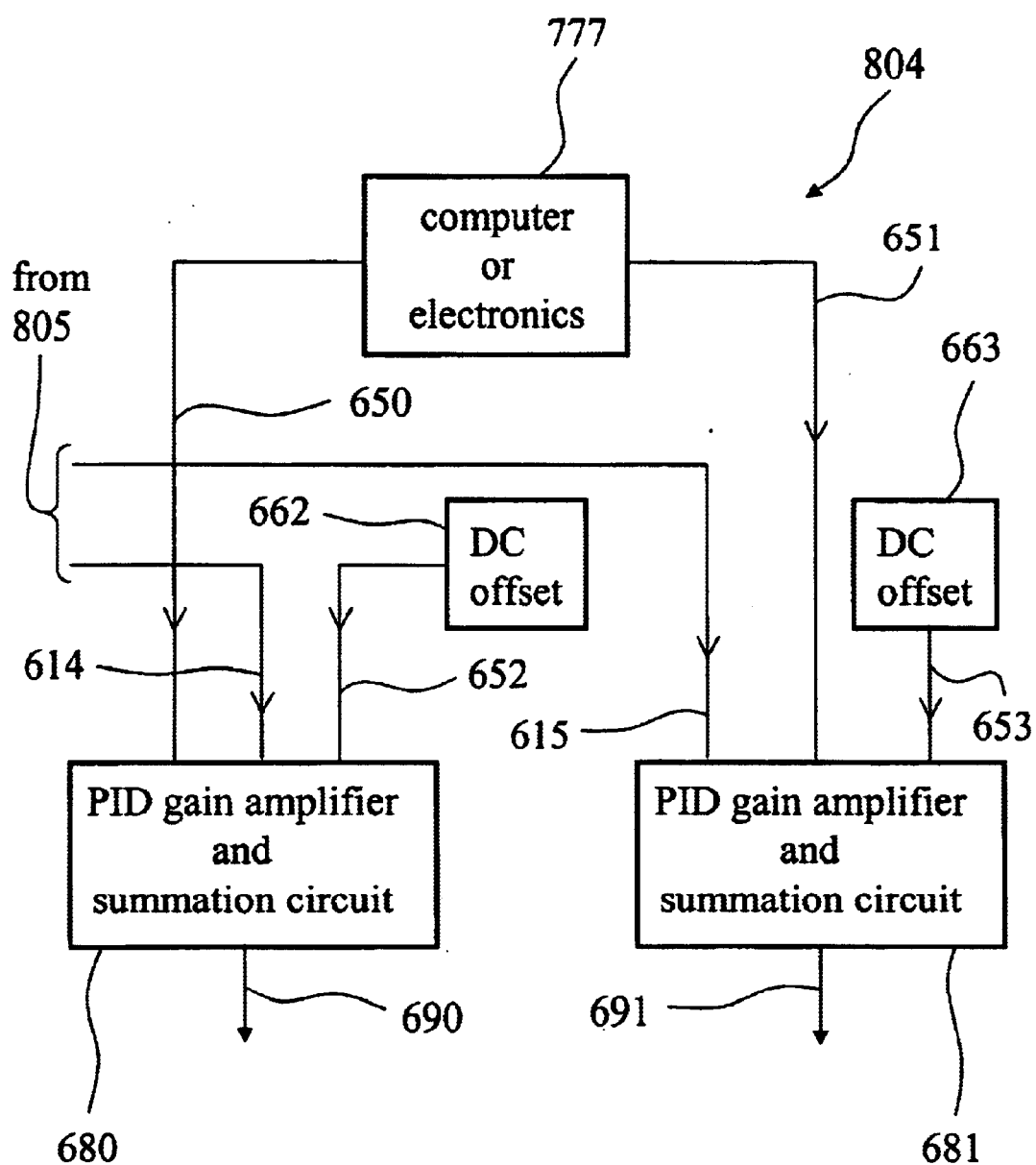
FIG. 3 is a functional block diagram of control module 804 that is fabricated in accordance with one embodiment of the present invention for use in the embodiment shown in FIG. 1.

FIG. 3 is a functional block diagram of control module 804 that is fabricated in accordance with one embodiment of the present invention for use in the embodiment shown in FIG. 1. As shown in FIG. 3, computer 777 (or conventional electronics circuit 777) generates OCT X scan signal 650 and OCT Y scan signal 651 (OCT X scan signals 650 and 651 are signals whose form depends on particular algorithms used to produce appropriate OCT scanning in the X and Y directions, respectively; and many methods are well known to those of ordinary skill in the art for generating such signals). As further shown in FIG. 3: (a) X position error signal 614 (generated in control module 805), OCT X scan signal 650, and DC offset signal 652 are applied as input to PID gain amplifier and summation circuit 680; and (b) Y position error signal 615 (generated in control module 805), OCT Y scan signal 651, and DC offset signal 653 are applied as input to PID gain amplifier and summation circuit 681. DC offset signals 652 and 653 may be used, for example, and without limitation, to: (a) calibrate embodiment 100; (b) set up initial X and Y offset positions for the tracking beam with respect to the scanning beam; and (c) reset embodiment 100 to adjust for drifts over time due to temperature variation, or other reasons. DC offset signals 652 and 653 are generated by DC offset modules 662 and 6663, respectively, in accordance with any one of a number of methods that are well known to those of ordinary skill in the art (for example, using conventional electronics or a computer such as, for example, a personal computer), and DC offset signals 652 and 653 may be varied in response to user input in accordance with any one of a number of methods that are well known to those of ordinary skill in the art. It should also be understood that appropriate scale factors may be applied to X position error signals 614 and 615, respectively, which scale factors may be determined by calibrating embodiment 100 to ensure that the tracking beam follows the reference tracking feature.

As is well known, PID gain amplifier summation circuits 680 and 681, in response to predetermined parameters, add their three inputs and generate signals 690 and 691, respectively, as output. The predetermined parameters: (a) enable PID gain amplifier summation circuits 680 and 681 to integrate the respective error signals over a predetermined length of time to identify and ignore short-lived changes, and thereby, prevent jitter from affecting the system; and (b) enable PID gain amplifier summation circuits 680 and 681 to take the derivative of the respective error signals so that the rate of change is larger than a predetermined amount, and thereby, prevent jitter from affecting the system.

Signals 690 and 691 output from PID gain amplifier summation circuits 680 and 681, respectively, are applied as input to scanner driver 803. Thus, in accordance with one embodiment of the present invention, signal 690 is applied as input to a galvanometer that drives the X-direction scanning mirror of the pair of mirrors 212 and 213, and signal 691 is applied as input to a galvanometer that drives the Y-direction scanning mirror of the pair of mirrors 212 and 213. In response, the X-direction scanning mirror scans the scanning beam along the X direction, and causes the scanning beam to follow the motion of the eye along the X direction. In addition, the Y-direction scanning mirror scans the scanning beam along the Y direction, and causes the scanning beam to follow the motion of the eye along the Y direction.

It should be clear to those of ordinary skill in the art that embodiments of the present invention are not limited to the use of a PID gain amplifier and summation circuit. In fact, further embodiments exist wherein the above-described operations carried out by the PID gain amplifier and summation circuit may be carried out using, for example, a computer such as a personal computer.

It should be understood that embodiments of the present invention are not limited to method or apparatus described above wherein: (a) the scanning motion of the scanning beam and the tracking motion of the scanning beam (i.e., the tracking motion of the scanning beam is movement of the scanning beam to cause it to track the detected motion) are both produced by driving a scanning mechanism in the scanning arm; and (b) the dithering motion of the tracking beam and the tracking motion of the tracking beam (i.e., the tracking motion of the tracking beam is movement of the tracking beam to cause it to track the detected motion) are both produced by driving a dither mechanism in the tracking arm. In fact, further embodiments exist wherein the tracking motion of the scanning beam and/or the tracking beam is provided by a separate tracking mechanism disposed in the scanning arm and/or the tracking arm, respectively. In fact, still further embodiments exist wherein the tracking motion of the scanning beam and the tracking beam may be carried out by a single tracking mechanism disposed in the path of the scanning beam and the tracking beams. In accordance with such further embodiments, the tracking signals would be distributed to the specific tracking mechanism(s) in a manner that should be clear to those of ordinary skill in the art in light of the discussion set forth above. Such tracking mechanisms could include paired reflectors of the type used to fabricate scanning mechanism 227 or dithering mechanism 329. In other words, one or more of the above-described embodiments comprise a tracking mechanism system that may include, for example and without limitation: (a) tracking being performed by the scanning mechanism in the scanning arm and by the dither mechanism in the tracking arm; (b) separate tracking mechanisms in the scanning arm and the tracking arm; or (c) one tracking mechanism that tracks the scanning beam and the tracking beam. Lastly, in accordance with such embodiments, dither mechanism 329 may be embodied, for example, utilizing resonant scanners or utilizing an embodiment disclosed in FIG. 3 of U.S. Pat. No. 6,325,512.

Although embodiments of the present invention described above in conjunction with FIGS. 1–3 work well with a roundish reference tracking feature such as, for example, and without limitation, an optic disk or a laser-induced retinal lesion, it has been discovered that they are not as reliable when utilized with a reference tracking feature such as a blood vessel junction (for example, a blood vessel junction might be utilized as a reference tracking feature, for example, and without limitation, whenever a roundish tracking feature is absent near a macular region, or whenever reflection from the optic disk is not very uniform). The problem occurs because phase and amplitude changes of a reflectometer signal that is modulated by blood vessels cannot be used to provide information about the direction of movement and the amount of displacement of the blood vessel junction whenever the tracking beam is dithered partially outside the blood vessel junction. In addition, tracking may be lost if eye movement is in a direction such that the tracking beam continues to dither within one of the blood vessels because, in such an instance, changes in phase or signal amplitude of the reflectometer signal may not be detected.

One or more further embodiments of the present invention solve the above-described problem, and enable tracking using a non-roundish reference tracking feature such as, for example, and without limitation, a blood vessel junction. In particular, one or more such further embodiments of the present invention enable tracking by scanning a tracking beam having a relatively small spot size. The spot size may be determined routinely by one of ordinary skill in the art without undue experimentation. For example, if the spot size is too small, there may not be enough reflection to provide a good signal. On the other hand, if the spot size is too large, there may not be enough contrast with the background to provide good tracking. A reasonable spot size is one having a diameter that is less than about ⅓ of a length across a cross section of the smallest blood vessel in the blood vessel junction. In accordance with one or more such further embodiments, a reference reflectometer signal is generated that for the reference tracking feature (i.e., the blood vessel junction) when the reference tracking feature is disposed at a fixed position and orientation (i.e., a calibration position). As will be described in detail below, in accordance with one or more embodiments of the present invention, a computer and/or an electronic system compares aspects of the reference reflectometer signal generated at the calibration position (i.e., calibration information) with aspects of a reflectometer signal generated after calibration, and generates correction signals that are used in the manner described below to provide tracking.

Figure 4:
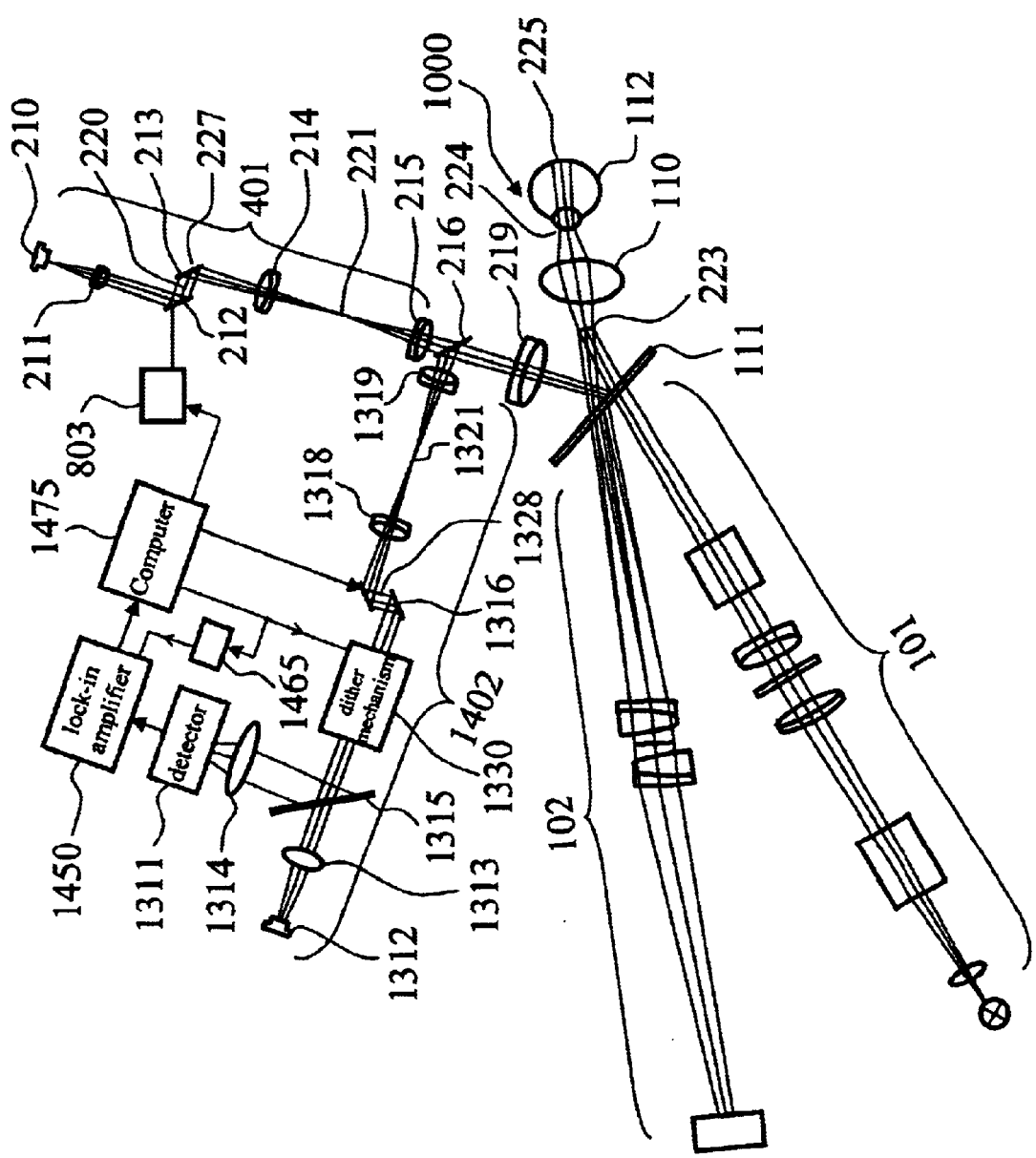
FIG. 4 shows a diagram of a portion of an alternative embodiment of the present invention, and various optical paths associated therewith.

FIG. 4 shows a diagram of a portion of alternative embodiment 1000 of the present invention, and various optical paths associated therewith. As shown in FIG. 4, fundus illumination apparatus 101, viewing apparatus 102, and OCT scanning arm 401 are the same as the similarly numbered apparatus described above in conjunction with FIG. 1. As further shown in FIG. 4, an embodiment of active tracking system 1402 comprises tracking beam radiation source 1312 which is, for example, and without limitation, a laser or a light emitting diode ("LED"), or any one of a number of other coherent or incoherent sources of radiation. In accordance with one such embodiment, the tracking beam output from tracking beam radiation source 1312 comprises radiation that can be used to detect changes in reflectance between the reference tracking feature and the surrounding area. In addition, it is preferred that such radiation comprises wavelengths not detected by an eye such as, for example, and without limitation, wavelengths centered about 880 nm. As further shown in FIG. 4, the tracking beam output from tracking beam radiation source 1312 is collimated by collimating lens system 1313 (as is well known to those of ordinary skill in the art, lens system 1313 may comprise one or more lenses). The collimated tracking beam passes through beamsplitter 1315 (for example, and without limitation, a 50/50 beamsplitter), and impinges upon dither mechanism 1330. In accordance one or more such embodiments, dither mechanism 1330 comprises a pair of orthogonally mounted (along X and Y directions, respectively) resonant scanners which are driven by a resonant scanner driver in a manner that is well known to those of ordinary skill in the art. In alternative such embodiments dither mechanism 1330 may be embodied utilizing the dither mechanism disclosed in FIG. 3 of U.S. Pat. No. 6,325,512.

As further shown in FIG. 4, the collimated tracking beam output from dither mechanism 1330 impinges upon tracking mechanism 1316 which directs the collimated tracking beam to a specific target destination. In accordance with one or more such embodiments of the present invention, tracking mechanism 1316 comprises reflectors that are orthogonally mounted on, for example, and without limitation, a pair of X-Y galvanometers in accordance with any one of a number of methods that are well known to those of ordinary skill in the art (for example, galvanometers with low armature inertia can be used to achieve a high-speed tracking response).

In accordance with this embodiment of the present invention, and as was described above in conjunction with FIG. 1, pivot point 1320 of tracking mechanism 1316 (i.e., in accordance with one embodiment, a middle point between the pair of tracking mirrors) is optically conjugated to pupil 224 of eye 112 by (a) one-to-one magnification, relay lens system pair 1318 and 1319; and (b) lens system 219 and ocular lens system 110. Thus, as was described in U.S. Pat. No. 5,506,634, there will be no vignetting in the tracking beam. As is well known to those of ordinary skill in the art, lens systems 1318 and 1319 may each comprise one or more lenses.

Then, as was described above in conjunction with FIG. 1, and in accordance with this embodiment of the present invention: (a) the collimated tracking beam output from tracking mechanism 1316 is focused by lens system 1318 to point 1321; (b) point 1321 is optically conjugated to aerial image plane 223 by relay lens system pair 1319 and 219; and (c) aerial image plane 223 is optically conjugated to retina 225 of eye 112 by ocular lens system 110 and the lens of eye 112.

As was described above in conjunction with FIG. 1, the tracking beam impinges upon retina 225, and retina 225 retro-reflects at least a portion of the tracking beam. The retro-reflected tracking beam is directed (through the same optical path that brought the tracking beam to eye 112 in the first place) to beamsplitter 1315. Beamsplitter 1315 directs the retro-reflected tracking beam to impinge upon lens system lens 1314 (as is well known to those of ordinary skill in the art, lens system 1314 may comprise one or more lenses), and lens system 1314 focuses the retro-reflected tracking beam upon detector 1311 (for example and without limitation, including a photodiode and conventional electronics to condition the signal for further processing in accordance with any one of a number of methods that are well known to those of ordinary skill in the art, for example, and without limitation, by amplification). The conditioned signal is then applied as input to dual channel, lock-in amplifier 1450.

In accordance with one or more such embodiments of the present invention, prior to utilizing one or more such embodiments to track motion of a particular eye, a calibration procedure is performed. A first step of the calibration procedure entails utilizing tracking mechanism 1316 to direct the tracking beam so that it impinges upon, for example, and without limitation, a center of a junction of three (or more) blood vessels. This first calibration step of aiming the tracking beam at a center of the junction of the blood vessels can be performed in accordance with any one of a number of methods that are well known to those of ordinary skill in the art. For example, this first calibration step can be performed: (a) by utilizing a beam of visible radiation emitted, for example, by a laser diode to aid an operator in adjusting the direction of the tracking beam in accordance with any one of a number of methods that are well known to those of ordinary skill in the art; or (b) by utilizing a CCD camera to display the reflected tracking beam to aid an operator in adjusting the direction of the tracking beam in accordance with any one of a number of methods that are well known to those of ordinary skill in the art.

A second step of the calibration procedure entails activating dither mechanism 1330 to cause the tracking beam to move about the center of the junction of the blood vessels in a predetermined pattern, for example, and without limitation, a circular scan. In accordance with one or more such embodiments of the present invention, dither mechanism 1330 produces a circular dither at the reference tracking feature in response to synchronized oscillatory signals having identical amplitudes and a phase difference of 90 degrees, for example, and without limitation, a cosine signal (i.e., $\cos(\omega t)$) and a sine signal (i.e., $\sin(\omega t)$). As a result, the $\cos(\omega t)$ and $\sin(\omega t)$ signals cause the tracking beam to be dithered at a frequency $\omega$, for example, and without limitation, that may be at least as high as 8.3 kHz.

Figure 5:
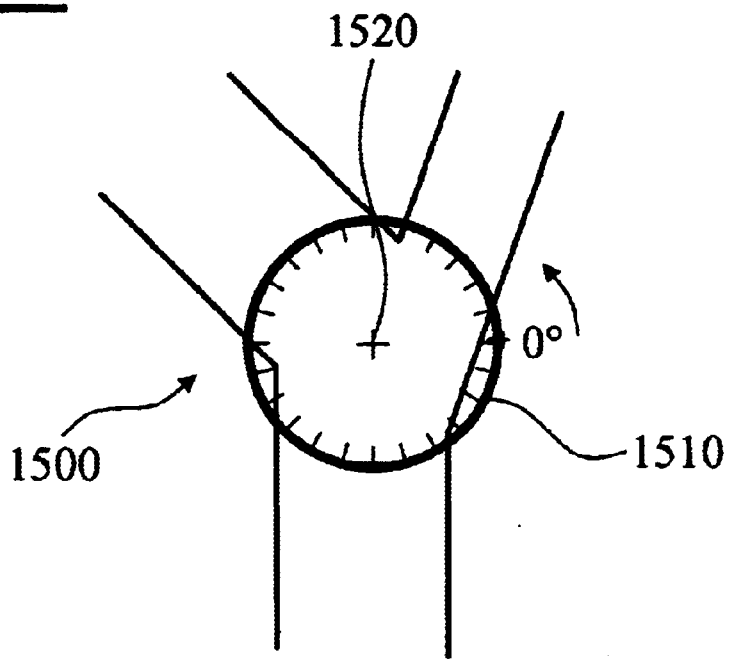
FIG. 5 shows a pictorial representation of a scan about a center of a junction of blood vessels to generate a calibration signal.
Figure 6:
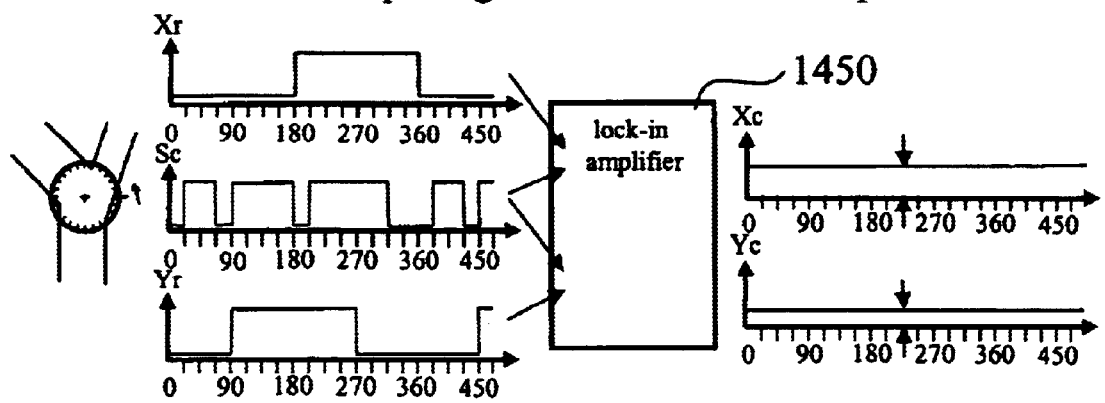
FIG. 6 shows a pictorial representation of scan signal Sc (obtained by scanning or dithering during a calibration procedure) that is input to a dual-channel, lock-in amplifier, along with reference signals Xr and Yr, to generate phase-shift signals Xc and Yc.

In accordance with one or more such embodiments, and as shown in FIG. 5, scanning circle 1510 has a larger diameter than blood vessel junction 1500, and is scanned, for example, and without limitation, in a counter-clockwise direction about center position 1520. Because of differences in reflectivity of radiation in the tracking radiation from the blood vessels and from surrounding retinal tissues, the retro-reflected tracking beam acquired by a reflectometer (comprised of beamsplitter 1315, lens system 1314, and detector 1311) will produce a modulated reflectometer output signal. FIG. 6 shows modulated reflectometer output signal Sc obtained by dithering, for example, and without limitation, about a position substantially at center 1520 of blood vessel junction 1500 shown in FIG. 5. As shown in FIG. 6, modulated reflectometer output signal Sc has three (or more) peaks that are modulated by the blood vessels shown in FIG. 5 for each periodic dithering cycle.

A third step of the calibration procedure entails applying Sc as input to dual-channel, lock-in amplifier 1450 (one could also use a pair of lock-in amplifiers) along with reference signals Xr and Yr, respectively, that are output from conventional electronics 1465. As shown in FIG. 6, reference signals Xr and Yr are TTL signals (for example, Xr is 90° shifted in phase with respect to Yr) that are generated by conventional electronics 1465 in response to the sinusoidal signals used to drive dither mechanism 1330.

In accordance with well known principles of operation of a lock-in amplifier, dual-channel, lock-in amplifier 1450 produces, as outputs, DC signals that are proportional to a phase shift between an input, for example, Sc, and reference signals, for example, Xr and Yr. Specifically, as shown in FIG. 6, in response to signals Sc, Xr, and Yr, dual-channel, lock-in amplifier 1450 produces, as outputs: (a) DC-level Xc (i.e. an "x phaseshift" obtained from scanning about center position 1520 that is formed using Sc and Xr); and (b) DC-level Yc (i.e., a "y phaseshift" obtained from scanning about center position 1520 that is formed using Sc and Yr). In accordance with one or more embodiments of the present invention, Xc and Yc applied as input to computer 1475, and computer 1475 stores them for later use. It should be understood that further embodiments exist wherein the above-described operations provided by lock-in amplifier 1450 (for example, multiplication of an input signal with a reference signal, and lowpass filtering the result) may be carried out using, for example, a computer such as a personal computer or a digital signal processor ("DSP").

Figure 7:
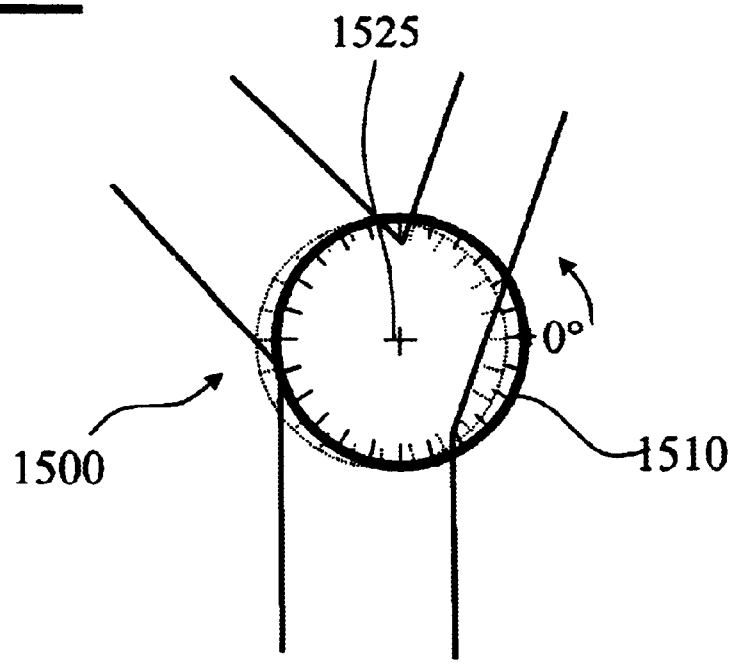
FIG. 7 shows a pictorial representation of a scan about a position displaced from the center of the junction of blood vessels to generate a displacement signal.
Figure 8:
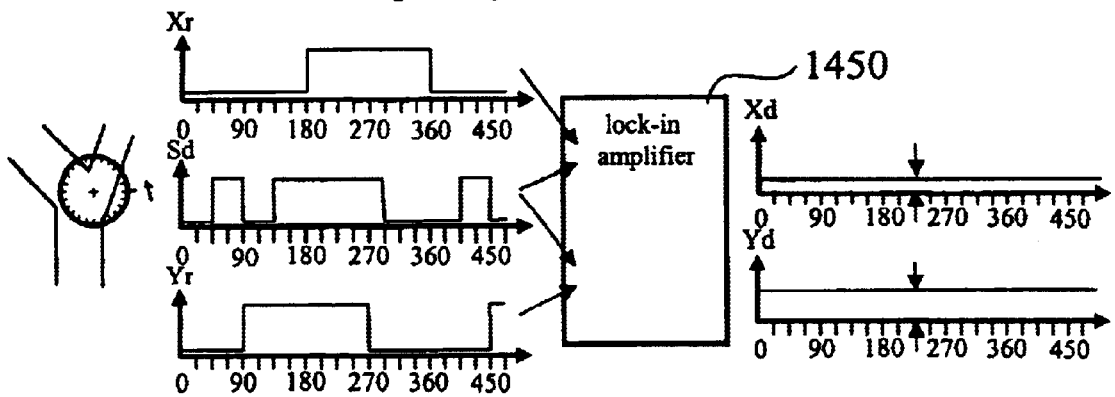
FIG. 8 shows a pictorial representation of scan signal Sd (obtained by scanning or dithering after the calibration procedure) that is input to the dual-channel, lock-in amplifier, along with reference signals Xr and Yr, to generate phase-shift signals Xd and Yd.

Whenever eye 112 moves after the calibration procedure has been carried out, scanning circle 1510 will be displaced relative to blood vessel junction 1500, and the tracking beam will be scanned across a different portion (referred to as a displaced position) of blood vessel junction 1510 (see FIG. 7 wherein scanning circle 1510 is scanned about point 1525 after eye 112 has moved). FIG. 8 shows a displaced reflectometer output signal Sd obtained by dithering about point 1525 shown in FIG. 7. As shown in FIG. 8, displaced reflectometer output signal Sd has a different shape and intensity distribution from that of Sc. In same manner as was described above with respect to the calibration procedure, Sd and reference signals Xr and Yr are applied as input to dual-channel, lock-in amplifier 1450. Further, in the same manner as was described above, and as shown in FIG. 8, in response to signals Sd, Xr, and Yr, dual-channel, lock-in amplifier 1450 produces, as outputs: (a) DC-level Xd (i.e., an "x phaseshift" obtained from scanning the tracking beam about position 1525 that is formed using Sd and Xr); and (b) DC-level Yd (i.e., a "y phaseshift" obtained from scanning the tracking beam about position 1525 that is formed using Sd and Yr). In accordance with one or more embodiments of the present invention, Xd and Yd are applied as input to computer 1475. Computer 1475 generates error signals Xe and Ye by subtracting previously stored signals (Xc and Yc) from (Xd and Yd). In particular, Xe=(Xd−Xc), and Ye=(Yd−Yc).

In accordance with one or more embodiments of the present invention, error signals Xe and Ye relate to a direction of eye movement that caused the displacement of blood vessel junction 1500. Further, after normalization or scaling by parameters that are determined by calibration procedures in accordance with any one of a number of methods that are well known to those of ordinary skill in the art to ensure that the tracking beam follows the reference tracking feature, Xe and Ye describe a vector direction of motion (−Xe, −Ye) that will track the eye movement.

As shown in FIG. 4, appropriate X and Y tracking correction signals are transmitted from computer 1475 to a driver (not shown) for tracking mechanism 1316. In response, the X-direction tracking mirror causes the tracking beam to follow movement of the eye along the X direction, and the Y-direction tracking mirror causes the tracking beam to follow movement of the eye along the Y direction. As was described above in conjunction with FIG. 2, the appropriate X and Y tracking correction signals may include X and Y DC offset signals that may be used, for example, and without limitation, to: (a) calibrate embodiment 1000; (b) set up initial X and Y offset positions for the tracking beam with respect to the scanning beam; and (c) reset embodiment 1000 to adjust for drifts over time due to temperature variation, or other reasons. The X and Y DC offset signals are generated in accordance with any one of a number of methods that are well known to those of ordinary skill in the art for example, by computer 1475, and the X and Y DC offset signals may be varied in response to user input in accordance with any one of a number of methods that are well known to those of ordinary skill in the art. In addition, as was described above, the appropriate X and Y correction signals may also be smoothed to remove jitter in accordance with any one of a number of methods that are well known to those of ordinary skill in the art.

In addition, computer 1475 transmits signals to scanner driver 803 to cause scanning mechanism 227 to scan and track movement of the eye (note that computer 1475 performs the functions provided by control module 804 described above in conjunction with FIG. 3).

It should be noted that although the above-described embodiments included computer 1475, embodiments of the present invention are not limited to use of a computer. In fact, further embodiments exist wherein all or portions of the functionality described above as being performed by computer 1475 are performed by electronic circuitry.

As one can readily appreciated from the above, whenever eye 112 moves, a scan is generated about a position that is different from center position 1520, and error signals Xe and Ye are generated (i.e., as long as the movement causes a displacement from the calibration position, signals Xd and/or Yd will be different from Xc and/or Yc, and Xe and/or Ye will be different from zero). Thus, as long as Xe and/or Ye are non-zero, tracking mechanism 1316 and drive scanning mechanism 227 will not stop tracking movement of eye 112. Further, whenever Xe and Ye are zero, no tracking will occur until eye 112 moves again.

The following describes further alternative embodiments of the present invention which modify the further embodiments described above (in particular, embodiment 1000 described above in conjunction with FIG. 4). In essence, such further alternative embodiments operate differently only in relation to how error signals Xe and Ye are generated. In particular, in accordance with such further alternative embodiments, a calibration procedure is carried out to develop a reference reflectometer output signal Sc in the same manner that was described above. However, instead of applying Sc as input to dual-channel, lock-in amplifier 1450, Sc is applied as input to, and stored in, computer 1475 (for example, Sc is stored for a predetermined number of 360° scans, such as one). Next, as was described above, whenever eye 112 moves from its calibration position, a displaced reflectometer output signal Sd is obtained in the same manner that was described above. However, instead of applying Sd as input to dual-channel, lock-in amplifier 1450, Sd is applied as input to computer 1475. Then, in accordance with such further alternative embodiments of the present invention, computer 1475 subtracts reference reflectometer output signal Sc from newly received, displaced reflectometer output signal Sd (for the same number of 360° scans). Then, the subtracted reflectometer output signal is applied as input to dual channel, lock-in amplifier 1450, along with clock signals Xr and Yr, to generate DC-level error signals Xe and Ye (these are the same as error signals Xe and Ye generated by embodiment 1000 described above in conjunction with FIG. 4). It should be understood that further embodiments exist wherein the above-described operations provided by dual-channel, lock-in amplifier 1450 (for example, multiplication of an input signal with a reference signal, and lowpass filtering the result) may be carried out using, for example, a computer such as a personal computer or a digital signal processor ("DSP"). Error signals Xe and Ye are then utilized in the same manner described above in conjunction with FIG. 4 to provide tracking.

It should be understood that the alternative embodiments of the present invention are not limited to method or apparatus wherein: (a) the scanning motion of the scanning beam and the tracking motion of the scanning beam (i.e., the tracking motion of the scanning beam is movement of the scanning beam to cause it to track the detected motion) are both produced by driving a scanning mechanism in the scanning arm; and (b) the dithering motion of the tracking beam and the tracking motion of the tracking beam (i.e., the tracking motion of the tracking beam is movement of the tracking beam to cause it to track the detected motion) are produced by driving a dither mechanism in the tracking arm and by driving a tracking mechanism in the tracking arm. In fact, further embodiments exist wherein the tracking motion of the scanning beam is provided by a separate tracking mechanism disposed in the scanning arm. In fact, still further embodiments exist wherein the tracking motion of the scanning beam and the tracking beam may be carried out by a single tracking mechanism disposed in the path of the scanning beam and the tracking beams. In accordance with such embodiments, the tracking signals would be distributed to the specific tracking mechanism(s) in a manner that should be clear to those of ordinary skill in the art in light of the discussion set forth above. Such tracking mechanisms could include paired reflectors of the type used to fabricate scanning mechanism 227 or tracking mechanism 1316. In other words, one or more of the above-described embodiments comprise a tracking mechanism system that may include, for example, and without limitation: (a) tracking being performed by a scanning mechanism in the scanning arm and by a tracking mechanism in the tracking arm; (b) separate tracking mechanisms in the scanning arm and the tracking arm; or (c) one tracking mechanism that tracks the scanning beam and the tracking beam.

Those skilled in the art will recognize that the foregoing description has been presented for the sake of illustration and description only. As such, it is not intended to be exhaustive or to limit the invention to the precise form disclosed. For example, although embodiments of the present invention were described in relation to obtaining OCT scan images of an eye, the present invention is not limited thereby, In particular, it is within the scope and spirit of the present invention to encompass method and apparatus for obtaining OCT images of any type of material such as, for example and without limitation, animal, human, and plant tissue. Advantageously, use of one or more embodiments of the present invention can utilize axial scan rates below about 500 Hz, including axial scan rates in a range from about 150 Hz to about 350 Hz.

Although the above-described embodiments of the present invention were described in relation to tracking assisted OCT applications, it should be understood that further embodiments of the present invention are not limited to tracking assisted OCT applications. In fact, one or more further embodiments of the present invention relate to method and apparatus for performing optical procedures using an active tracking system to lock an optical beam on desired features, such optical procedures including laser surgical applications such as, for example and without limitation, laser photo-coagulation procedures, laser refractive surgical procedures (for example, laser corneal ablation procedures), and so forth. For example, such laser photo-coagulation procedures include laser photo-coagulation of the retina, for example, see an article by Espen Naess et al. entitled "Computer-assisted laser photo-coagulation of the retina-a hybrid approach" by E. Naess et al., *J. of Biomedical Optics,* 7(2) April, 2002, pp. 179–189. In addition, such laser surgical applications further include laser refractive surgical procedures.

In accordance with one or more embodiments of the present invention that relate to laser surgical applications such as laser photo-coagulation of the retina, tracking is provided by tracking blood vessel junctions in the retina as described above in conjunction with FIGS. 4–8. Further, in accordance with such embodiments of the present invention, OCT scanning arm 401 shown in FIG. 4 is replaced by a laser photo-coagulation beam arm that is fabricated in accordance with any one of a number of methods that are well known to those of ordinary skill in the art, and that focuses a laser photo-coagulation beam at the retina of eye 112 in accordance with any one of a number of methods that are well known to those of ordinary skill in the art. In accordance with such embodiments, active tracking system 1402 described above in conjunction with FIGS. 4–7 is directed to track using, for example, and without limitation, a blood vessel junction on the retina as a reference tracking feature. Still further, an appropriate tracking mechanism system may be fabricated in accordance with the teaching described above.

In accordance with one or more embodiments of the present invention that relate to a laser surgical applications such as laser refractive surgical procedures: (a) OCT scanning arm 401 shown in FIG. 4 is replaced by a laser surgical beam apparatus that focuses a laser corneal ablation beam at the cornea of eye 112 in accordance with any one of a number of methods that are well known to those of ordinary skill in the art; (b) fundus illumination apparatus 101 and viewing apparatus 102 shown in FIG. 4 may be eliminated; and (c) active tracking system 1402 described above in conjunction with FIGS. 4–7 is directed to track using as a reference tracking feature: (i) a pupil-iris boundary, (ii) an iris-sclera boundary, or (iii) a blood vessel junction on the sclera. In addition, in accordance with such embodiments, a focal length of ocular lens system 110 shown in FIG. 4 is adjusted in accordance with any one of a number of methods that are well known to those of ordinary skill in the art so that the tracking beam will be focused on the above-identified reference tracking feature. Further, an appropriate tracking mechanism system may be fabricated in accordance with the teaching described above.

What is claimed is:

1. An optical coherence tomography ("OCT") application apparatus which performs an OCT application on an object, which OCT application apparatus comprises:
    an OCT scanning apparatus which outputs a scanning beam of OCT scanning radiation; and
    an active tracking system that generates and scans a tracking beam of tracking radiation in a predetermined pattern over a region; wherein the active tracking system comprises an analysis system that:
        when the object is at a calibration position, scans the tracking beam about an irregular reference tracking feature in the region, and detects a calibration retro-reflected tracking beam to form calibration information;
        after the calibration information is formed, scans the tracking beam over the region, detects a displacement retro-reflected tracking beam, and analyzes the detected displacement retro-reflected tracking beam together with the calibration information to detect movement of the object;
        generates tracking signals; and
        applies the tracking signals to a tracking mechanism system to cause the tracking beam and the scanning beam to follow movement of the object.

2. The OCT application apparatus of claim 1 wherein the active tracking system includes a dither mechanism that scans the tracking beam in a predetermined shape.

3. The OCT application apparatus of claim 1 wherein the analysis system forms calibration information by applying a signal representative of the calibration retro-reflected tracking beam as input to a signal analyzer to form calibration DC output signals.

4. The OCT application apparatus of claim 3 wherein the analysis system analyzes the detected displacement retro-reflected tracking beam together with the calibration information by applying a signal representative of the displacement retro-reflected tracking beam as input to the signal analyzer to determine displacement DC output signals.

5. The OCT application apparatus of claim 4 wherein the analysis system further analyzes the detected displacement retro-reflected tracking beam by subtracting the calibration DC output signals from the displacement DC output signals to form the tracking signals.

6. The OCT application apparatus of claim 5 wherein the signal analyzer includes a lock-in amplifier.

7. The OCT application apparatus of claim 1 wherein the analysis system forms calibration information saving a signal representative of the calibration retro-reflected tracking beam for a predetermined period.

8. The OCT application apparatus of claim 7 wherein the analysis system analyzes the detected displacement retro-reflected tracking beam together with the calibration information by subtracting the signal representative of the calibrated retro-reflected tracking beam from a signal representative of the displacement retro-reflected tracking beam over the predetermined period to form a difference signal.

9. The OCT application apparatus of claim 8 wherein the analysis system further analyzes the detected displacement retro-reflected tracking beam by applying the difference signal as input to a signal analyzer to form the tracking signals.

10. The OCT application apparatus of claim 1 wherein the tracking mechanism system includes a scanning beam tracking mechanism and a tracking beam tracking mechanism.

11. The OCT application apparatus of claim 1 wherein the tracking mechanism system includes a scanning beam and tracking beam tracking mechanism.

12. The OCT application apparatus of claim 1 wherein the irregular reference tracking feature includes a blood vessel junction.

13. The OCT application apparatus of claim 12 wherein the predetermined pattern is a circular scan.

14. An OCT application method which comprises steps of:
    outputting a scanning beam of OCT scanning radiation; and
    generating and scanning a tracking beam of tracking radiation in a predetermined pattern over a region including an irregular reference tracking feature;
    wherein:
        when the object is at a calibration position, scanning the tracking beam about an irregular reference tracking feature in the region, and detecting a retro-reflected tracking beam, and forming calibration information;
        after the calibration information is formed, scanning the tracking beam over the region, detecting a retro-reflected tracking beam, and analyzing the detected retro-reflected tracking beam together with the calibration information to detect movement of the object; and
        generating tracking signals; and
        applying the tracking signals to a tracking mechanism system to cause the tracking beam and the scanning beam to follow movement of the object.

15. An apparatus that performs an optical procedure on an object, which apparatus comprises:
- an optical procedure apparatus that outputs a procedure beam of optical radiation; and
- an active tracking system that generates and scans a tracking beam of tracking radiation in a predetermined pattern over a region; wherein the active tracking system comprises an analysis system that:
  - when the object is at a calibration position, scans the tracking beam about an irregular reference tracking feature in the region, and detects a calibration retro-reflected tracking beam to form calibration information;
  - after the calibration information is formed, scans the tracking beam over the region, detects a displacement retro-reflected tracking beam, and analyzes the detected displacement retro-reflected tracking beam together with the calibration information to detect movement of the object;
  - generates tracking signals; and
  - applies the tracking signals to a tracking mechanism system to cause the tracking beam and the procedure beam to follow movement of the object.

16. The apparatus of claim 15 wherein the optical procedure apparatus is a laser photo-coagulation apparatus; and the procedure beam is a laser photo-coagulation laser beam.

17. The apparatus of claim 15 wherein the optical procedure apparatus is a laser refractive surgical apparatus; and the procedure beam is a laser ablation beam.

18. The apparatus of claim 15 wherein the active tracking system includes a dither mechanism that scans the tracking beam in a predetermined shape.

19. The apparatus of claim 15 wherein the analysis system forms calibration information by applying a signal representative of the calibration retro-reflected tracking beam as input to a signal analyzer to form calibration DC output signals.

20. The apparatus of claim 19 wherein the analysis system analyzes the detected displacement retro-reflected tracking beam together with the calibration information by applying a signal representative of the displacement retro-reflected tracking beam as input to the signal analyzer to determine displacement DC output signals.

21. The apparatus of claim 20 wherein the analysis system further analyzes the detected displacement retro-reflected tracking beam by subtracting the calibration DC output signals from the displacement DC output signals to form the tracking signals.

22. The apparatus of claim 21 wherein the signal analyzer includes a lock-in amplifier.

23. The apparatus of claim 15 wherein the analysis system forms calibration information saving a signal representative of the calibration retro-reflected tracking beam for a predetermined period.

24. The apparatus of claim 23 wherein the analysis system analyzes the detected displacement retro-reflected tracking beam together with the calibration information by subtracting the signal representative of the calibrated retro-reflected tracking beam from a signal representative of the displacement retro-reflected tracking beam over the predetermined period to form a difference signal.

25. The apparatus of claim 24 wherein the analysis system further analyzes the detected displacement retro-reflected tracking beam by applying the difference signal as input to a signal analyzer to form the tracking signals.

26. The apparatus of claim 15 wherein the tracking mechanism system includes a scanning beam tracking mechanism and a tracking beam tracking mechanism.

27. The apparatus of claim 15 wherein the tracking mechanism system includes a scanning beam and tracking beam tracking mechanism.

28. The apparatus of claim 15 wherein the irregular reference tracking feature includes a blood vessel junction.

29. The apparatus of claim 28 wherein the predetermined pattern is a circular scan.

* * * * *